US010073062B2

(12) United States Patent
Bueno et al.

(10) Patent No.: US 10,073,062 B2
(45) Date of Patent: Sep. 11, 2018

(54) SYSTEM AND METHOD FOR INSPECTING FLANGE CONNECTIONS

(71) Applicant: General Electric Company, Schenectady, NY (US)

(72) Inventors: Manuel Kenneth Bueno, Syracuse, NY (US); Robert Martin Roney, Jr., Schoharie, NY (US); Willis James Perry, Lewistown, PA (US); Robert Charles Shaffer, Reedsville, PA (US); Richard Michael Hatley, Morristown, NJ (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 302 days.

(21) Appl. No.: 14/846,274

(22) Filed: Sep. 4, 2015

(65) Prior Publication Data
US 2016/0069839 A1    Mar. 10, 2016

Related U.S. Application Data

(60) Provisional application No. 62/046,676, filed on Sep. 5, 2014.

(51) Int. Cl.
| | |
|---|---|
| *G01N 29/44* | (2006.01) |
| *G01N 29/26* | (2006.01) |
| *G01N 29/04* | (2006.01) |

(52) U.S. Cl.
CPC ......... *G01N 29/043* (2013.01); *G01N 29/262* (2013.01); *G01N 29/4427* (2013.01);
(Continued)

(58) Field of Classification Search
CPC .............. G01N 29/043; G01N 29/262; G01N 29/4427; G01N 2291/106; G01N 2291/2691; G01N 2291/044
(Continued)

(56) References Cited

U.S. PATENT DOCUMENTS

| | | | | |
|---|---|---|---|---|
| 7,543,512 B2 * | 6/2009 | Smith | ..................... | E21B 47/01 73/865.8 |
| 7,624,510 B2 * | 12/2009 | Ferrari | ................... | G01B 21/04 33/503 |

(Continued)

FOREIGN PATENT DOCUMENTS

| | | | |
|---|---|---|---|
| CN | 102914593 | * | 2/2013 |
| JP | 2000338291 A | * | 12/2000 |

*Primary Examiner* — J M Saint Surin
(74) *Attorney, Agent, or Firm* — Mintz Levin Cohn Ferris Glovsky and Popeo, P.C.

(57) ABSTRACT

A system includes a probe assembly configured to inspect components of an assembled flange connection when the probe assembly is disposed within a bore of the components. The probe assembly includes a shaft configured to be aligned with an axis of the assembled flange connection, one or more ultrasound probes coupled to the shaft, and one or more encoders. The one or more ultrasound probes are configured to interface with an interior surface of the bore of the components, to emit ultrasound signals into the components, and to receive ultrasound signals from the components. The one or more encoders are coupled to the shaft and are configured to determine a position of the one or more ultrasound probes relative to a reference point of the assembled flange connection during an inspection of components of the assembled flange connection.

20 Claims, 6 Drawing Sheets

(52) U.S. Cl.
CPC . *G01N 2291/044* (2013.01); *G01N 2291/106* (2013.01); *G01N 2291/2691* (2013.01)

(58) Field of Classification Search
USPC .......................................................... 73/628
See application file for complete search history.

(56) References Cited

U.S. PATENT DOCUMENTS

| | | | |
|---|---|---|---|
| 9,134,278 B2* | 9/2015 | Klopffer | F16L 11/083 |
| 2007/0256862 A1* | 11/2007 | Lund | G01N 29/04 |
| | | | 175/39 |
| 2012/0215348 A1 | 8/2012 | Skrinde | |

* cited by examiner

SYSTEM AND METHOD FOR INSPECTING FLANGE CONNECTIONS

CROSS REFERENCE TO RELATED APPLICATION

This application claims priority from and the benefit of U.S. Provisional Application Ser. No. 62/046,676, entitled "SYSTEM AND METHOD FOR INSPECTING FLANGE CONNECTIONS", filed Sep. 5, 2014, which is hereby incorporated by reference in its entirety.

BACKGROUND

The subject matter disclosed herein relates to non-destructive inspection, and more specifically to a system and method for inspection of flange connections of a hydrocarbon extraction system.

Components of the hydrocarbon extraction systems may be located in onshore, offshore, subsea, or subterranean environments. Hydrocarbon extraction systems convey various fluids between components via tubular members. The conveyed fluids may be pressurized relative to the external environment of the components or other tubular members. Some components of the hydrocarbon extraction system are coupled to one another via flange connections. The components and flange connections are subjected to various loads and environmental conditions during operation in the hydrocarbon extraction system. Some components may be utilized with another hydrocarbon extraction system if the components pass an inspection and satisfy known standards. Unfortunately, traditional inspection methods involve disassembling components and flange connections, which can be expensive and time consuming. Additionally, repeated assembly and disassembly may increase wear on components and the flange connections.

BRIEF DESCRIPTION

Certain embodiments commensurate in scope with the present disclosure are summarized below. These embodiments are not intended to limit the scope of the claim, but rather these embodiments are intended only to provide a brief summary of the present disclosure. Indeed, embodiments of the present disclosure may encompass a variety of forms that may be similar to or different from the embodiments set forth below.

In a first embodiment, a system includes a probe assembly configured to inspect components of an assembled flange connection. The probe assembly includes a shaft configured to be aligned with an axis of the flange connection, one or more ultrasound probes coupled to the shaft, and one or more encoders. The one or more ultrasound probes are configured to interface with a bore of the components, to emit ultrasound signals into the components of the assembled flange connection, and to receive ultrasound signals from the components of the assembled flange connection. The one or more encoders are configured to determine a position of the one or more ultrasound probes relative to a reference point of the assembled flange connection during an inspection of components of the assembled flange connection.

In another embodiment, a controller is coupled to a probe assembly configured to be disposed within a bore of an assembled flange connection. The controller is configured to control axial movement of the probe assembly within the bore of the assembled flange connection and to control circumferential movement of the probe assembly within the bore of the assembled flange connection. The controller is also configured to control an ultrasound inspection of an interior surface of the bore. The ultrasound inspection includes emitting ultrasound signals from one or more probes of the probe assembly into the components, receiving ultrasound signals with the one or more probes of the probe assembly, and comparing the received ultrasound signals to baseline data for the assembled flange connection.

In another embodiment, an inspection method includes inserting a probe assembly into a bore of an assembled stack of components from a hydrocarbon extraction system, emitting ultrasound signals from the probe assembly into the components of the assembled stack, receiving ultrasound signals at the probe assembly, and generating a model of the assembled flange connection of the assembled stack based at least in part on the received ultrasound signals. The assembled stack of components includes the assembled flange connection between the components. The received ultrasound signals are reflected from the components of the assembled stack.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

Figure 1:
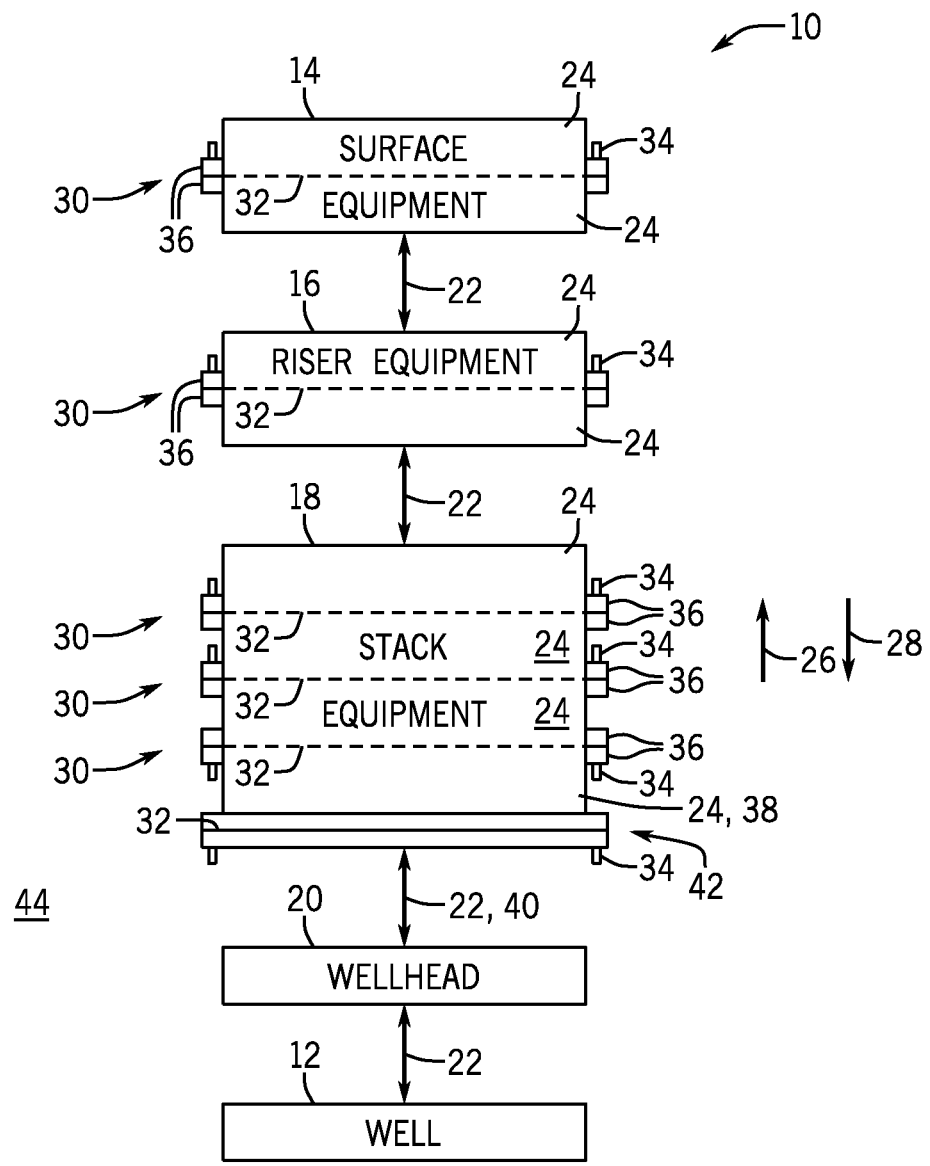
FIG. 1 is a block diagram of an embodiment of a hydrocarbon extraction system with some components coupled via flange connections.

A hydrocarbon extraction system 10 is illustrated in FIG. 1. The hydrocarbon extraction system 10 facilitates extraction of a hydrocarbon resource, such as oil or natural gas, from a well 12. The hydrocarbon extraction system 10 includes a variety of equipment, including surface equipment 14, riser equipment 16, and stack equipment 18, for extracting the resource from the well 12 via a wellhead 20. The hydrocarbon extraction system 10 may be employed in a variety of drilling or extraction applications, including onshore and offshore, i.e., subsea, drilling applications. For example, in a subsea resource extraction application, the surface equipment 14 is mounted to a drilling rig above the surface of the water, the stack equipment 18 is coupled to the wellhead 20 proximate to the sea floor, and the surface equipment 14 is coupled to the stack equipment 18 via the riser equipment 16. Connectors, illustrated by arrows 22, may facilitate coupling the equipment packages (e.g., surface equipment 14, riser equipment, 16, stack equipment 18, wellhead 20) of the hydrocarbon extraction system 10 to one another. Additionally, or in the alternative, connectors 22 may facilitate coupling of components within an equipment package to one another. Embodiments of the connector 22 may include, but are not limited to, an H-4® subsea connector, available from Vetco Gray of Houston, Tex.

The various equipment portions (e.g., surface equipment 14, riser equipment 16, stack equipment 18, wellhead 20) of the hydrocarbon extraction system 10 may include a variety of components 24. For example, the surface equipment 14 may include a variety of devices and systems, such as pumps, power supplies, cable and hose reels, control units, a diverter, a rotary table, and the like. Similarly, the riser equipment 16 may also include a variety of components, such as riser joints, valves, control units, and sensors, among others. In some embodiments, the riser equipment 16 may include a lower marine riser package (LMRP). The riser equipment 16 facilitates transmission of the extracted resource to the surface equipment 14 from the stack equipment 18 and the well 12. The stack equipment 18 also includes a number of components, such as one or more blowout preventers (BOPs), a subsea manifold, and/or production trees (e.g., completion or "Christmas" trees) for extracting the desired resource from the wellhead 20 and transmitting it to the surface equipment 14 and the riser equipment 16. The desired resource extracted from the wellhead 20 is transmitted to the surface equipment 14 generally in an upward direction 26. As utilized herein, a downward direction 28 is hereby defined as opposite the upward direction 26, such that the downward direction 28 is the general direction from the surface equipment 14 to the well 12. As may be appreciated, the upward direction 26 and the downward direction 28 are generally parallel to an axis of each component 24.

Some of the components 24 are coupled to one another via flange connections 30, thereby forming flange seals 32 between the respective components 24. The flange connections 30 may secure the respective components 24 together via fasteners 34 that at least partially extend through flanges 36 of one or both components 24 of the flange connection 30. In some embodiments, a component 38 (e.g., blowout preventer) is coupled to a connector 40 (e.g., H-4® subsea connector) via a flange connection 42.

As may be appreciated, the desired resource extracted from the wellhead 20 is transferred in the upward direction 26 through the equipment of the hydrocarbon extraction system 10 such that the desired resource is isolated from the environment 44 (e.g., subsea environment). The flange seals 32 enable the desired resource to be isolated from the environment 44 at each flange connection 30. For example, the flange seals 32 facilitate the isolation of the desired resource at a high temperature and/or a high pressure relative to the environment 44.

Some components 24 of the hydrocarbon extraction system 10 may be utilized in other hydrocarbon extraction systems during the serviceable life of the respective components 24. For example, upon completion of use of the stack equipment 18 in a first hydrocarbon extraction system 10 at a first well 12, at least some of the components 24 of the stack equipment 18 may be utilized in a second hydrocarbon extraction system at a second well. Traditionally, the components of the stack equipment 18 are brought to the surface (e.g., oil rig, surface vessel) so that the components 24 may be disassembled from one another for inspection and/or certification for additional service. The inspection may be performed at a site remote from the hydrocarbon extraction system 10 and the wellhead 20. Traditional inspections of the components 24 may include penetrant testing and/or magnetic particle testing of the flanges 36, the flange seals 32, and the fasteners 34. As may be appreciated, disassembly of the flange connections 30 may be time consuming. Additionally, disassembly and reassembly of the flange connections 30 may increase wear on the flange seals 32, the fasteners 34, and the flanges 36 of the components 24.

Figure 2:
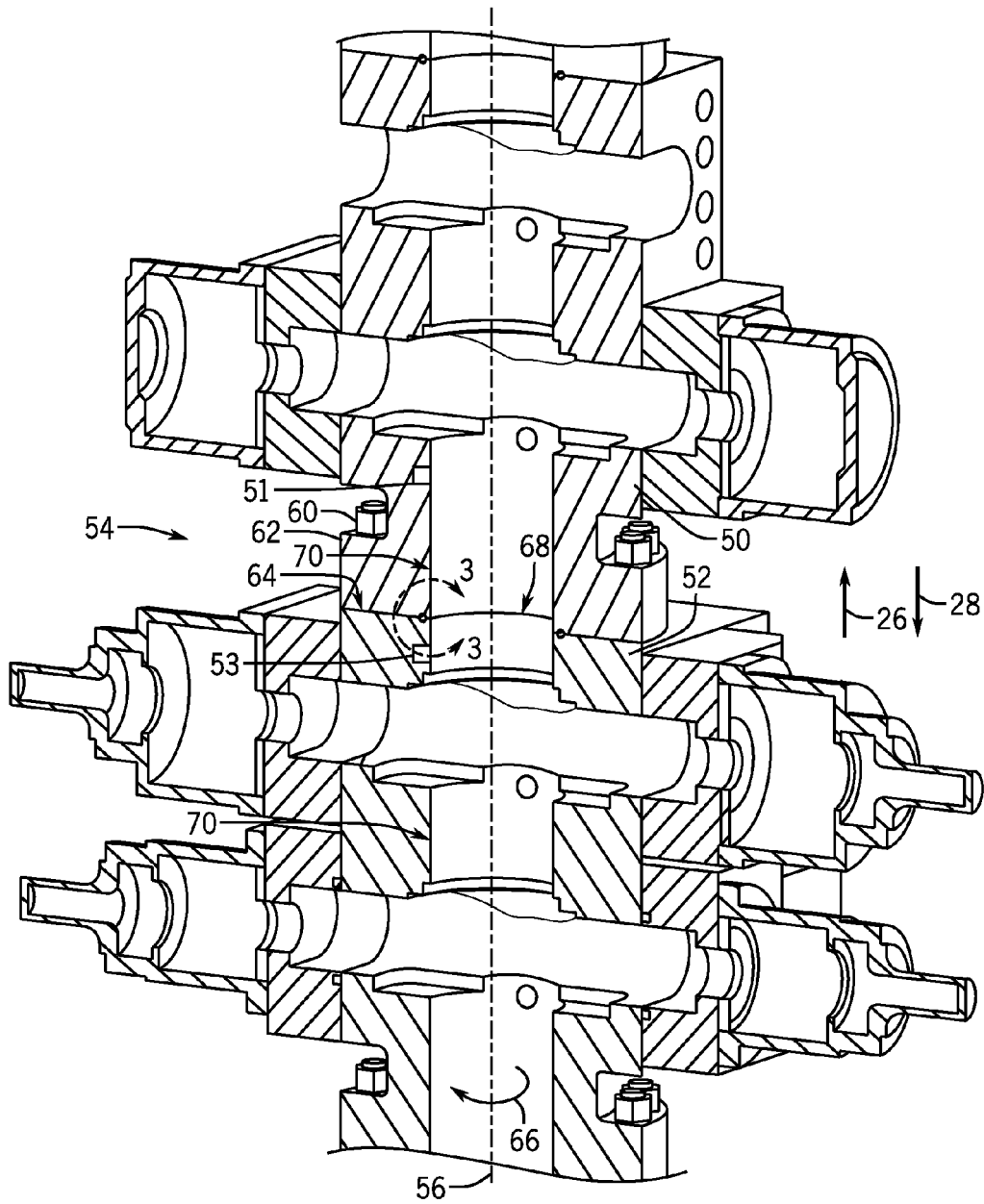
FIG. 2 is a cross-sectional view of an embodiment of a stack of a hydrocarbon extraction system with flange connections.

FIG. 2 is cross-sectional view of an embodiment of a portion of the stack equipment 18 of the hydrocarbon extraction system 10 of FIG. 1. A first component 50 of the stack equipment 18 is coupled to a second component 52 (e.g., blow out preventer (BOP)) via a flange connection 54. Both the first component 50 and the second component 52 are disposed about an axis 56 through a bore 58. In some embodiments, the first component 50 may be identified by a first identifier 51, and the second component 52 may be identified by a second identifier 53. The first and second identifiers 51, 53 may include, but are not limited to, serial numbers, bar codes, radio frequency identification (RFID) tags or chips, distinguishing part geometries, or any combination thereof. In some embodiments, the first and second identifiers 51, 53 are embedded within the respective components 50, 52.

The bore 58 facilitates fluid communication between the wellhead 20 and the surface equipment 14, such as for hydrocarbon flows, mud, or hydraulic fluids. A plurality of fasteners 60 (e.g., bolts, studs) extend through a flange 62 of the first component 52 and couple with a second surface 64 of the second component 52. The flange 62 extends in a circumferential direction 66 about the bore 58, and the plurality of fasteners 60 are disposed circumferentially about the axis 56 to secure the first component 50 to the second component 52. That is, the plurality of fasteners 60 may urge the first component 50 and the second component 52 towards each other such that a first surface 68 of the first component 50 interfaces with the second surface 64 of the second component 52.

Figure 3:
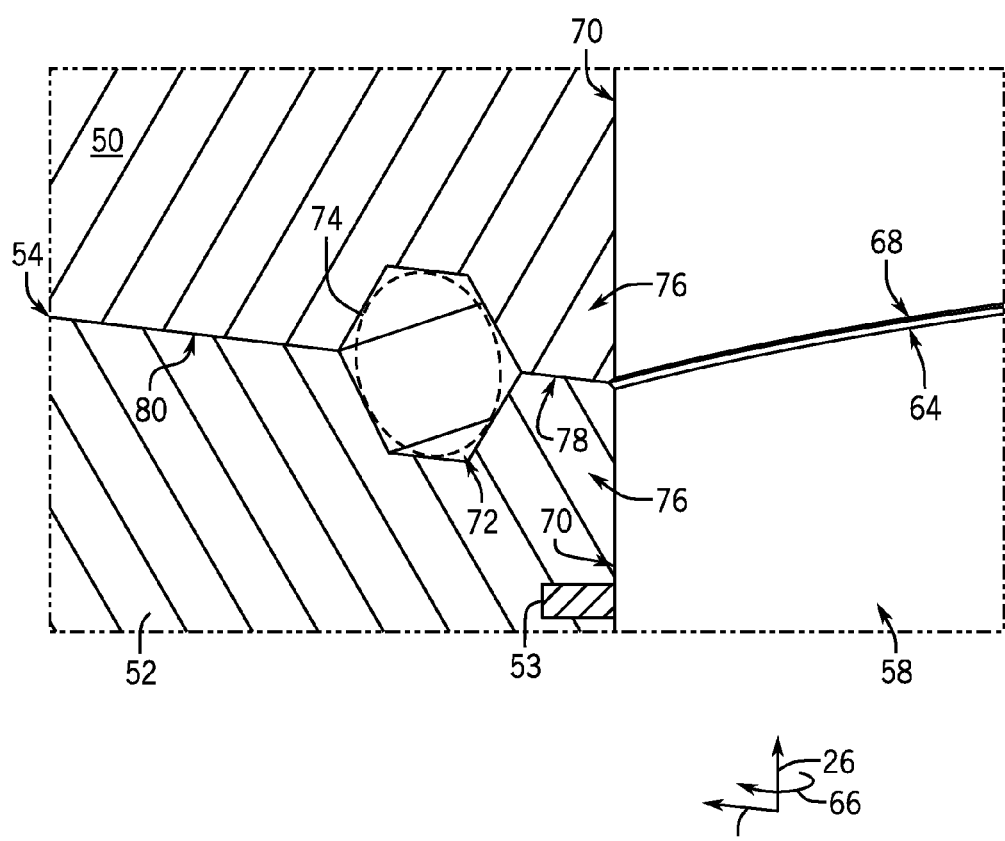
FIG. 3 is a cross-sectional view of an embodiment of a flange seal of a flange connection, taken along line 3-3 of FIG. 2.

FIG. 3 is a cross-sectional view of an embodiment of the flange connection 54 between the first component 50 and the second component 52, taken along line 3-3 of FIG. 2. Interior surfaces 70 of the first and second components 50, 52 form the bore 58 through the respective components 50, 52 of the assembled stack equipment 18. The first and second components 50, 52 may form a seal passage 72 near the interior surfaces 70 that extends in the circumferential direction 66 about the interior surfaces 70 (e.g., around the bore 58). The seal passage 72 is disposed in a radial direction 73 outside the interior surfaces 70. Recesses, grooves, or depressions in the first component 50 and/or the second component 52 form the seal passage 72. The shape of the seal passage 72 may include, but is not limited to a circle, a semicircle, an ellipse, a rectangle, a pentagon, a hexagon, an octagon, and so forth. The seal passage 72 is configured to receive a seal 74, such as an elastomeric seal, O-ring, C-ring, gasket, and so forth. As may be appreciated, the seal 74 provides flexibility to the flange connection 54 that enables fluids (e.g., hydrocarbons, oils, gases, slurries) within the bore 58 to remain isolated from the external environment 44 about the components 50, 52 despite some relative movement between the first and second components 50, 52 in the circumferential direction 66, the radial direction 73, or the axial 104. FIG. 3 illustrates an embodiment of the seal 74 with the dashed cross-section of a circular seal (e.g., O-ring). A lip portion 76 is radially disposed between the seal passage 72 and the interior surfaces 70 about the bore 58. The lip portion 76 may include portions of the first component 50 and the second component 52. Additionally, or in the alternative, the lip portion 76 may only include portions of the first component 50, or may only include portions of the second component 52. A lip interface 78 between the first surface 68 and the second surface 64 at the lip portion 76 facilitates the isolation of the bore 58 from the seal passage 72, and a body interface 80 facilitates the isolation of the seal passage 72 and the bore 58 from the external environment 44.

Various factors may affect the integrity and effectiveness of the flange connection 54 to isolate the bore 58 from the external environment 44 and to secure the first component 50 to the second component 52. The desired strength of portions of the first and second components 50, 52 is based at least in part on operating conditions of the hydrocarbon extraction system. The operating conditions may include, but are not limited to, the composition of the extracted resource, the pressure of the extracted resource, the external environment, the depth of the component when installed, and so forth. The strength of a component may be affected by flaws of the interior surfaces 70, the lip portion 76, the seal passage 76, the seal 74, or any combination thereof. Flaws may include, but are not limited to porosity, cracks (e.g., surface cracks or subsurface cracks), wear, or any combination thereof. Additionally, or in the alternative, flaws may affect the pressures at which the flange connection 54 between the first and second components 50, 52 forms an effective seal to isolate the bore 58 from the seal passage 72 and/or the external environment 44. Furthermore, flaws in the fasteners 60 of the flange connection 54 may affect the magnitude and the distribution about the axis 56 of a sealing force between the first component 50 and the second component 52.

The first and second components 50, 52 may be inspected and/or certified prior to utilization in a hydrocarbon extraction system 10. For example, the first and second components 50, 52 may be inspected and/or certified after manufacture and prior to installation in a first hydrocarbon extraction system. After utilization of the first and second components 50, 52 in the first hydrocarbon extraction system, it may be desirable for the first and second components 50, 52 to be installed in a second hydrocarbon extraction system. However, standards or regulations may require re-inspection and/or re-certification of the first and second components 50, 52 before utilization in the second hydrocarbon extraction system. For example, re-inspection and/or re-certification may identify flaws (e.g., porosity, cracks, wear) of portions of the first and second components 50, 52. Systems and methods described herein facilitate inspection of portions of the first and second components 50, 52 while the first and second components 50, 52 are assembled without disassembly of the flange connection 54. For example, a probe assembly discussed herein may utilize one or more ultrasound probes to inspect portions of the assembled first and second components 50, 52 of the flange connection 54. In some embodiments, probe assemblies may utilize one or more phased arrays of ultrasound probes. Accordingly, the probe assembly enables non-destructive testing of assembled flange connection 54, thereby reducing the cost, labor, and time of assembly and disassembly of the flange connection 54 with traditional inspection methods. Furthermore, a probe assembly may enable multiple components and multiple flange connections assembled together in series to be inspected at substantially the same time, thereby further reducing the cost, labor, and time of inspection.

Figure 4:
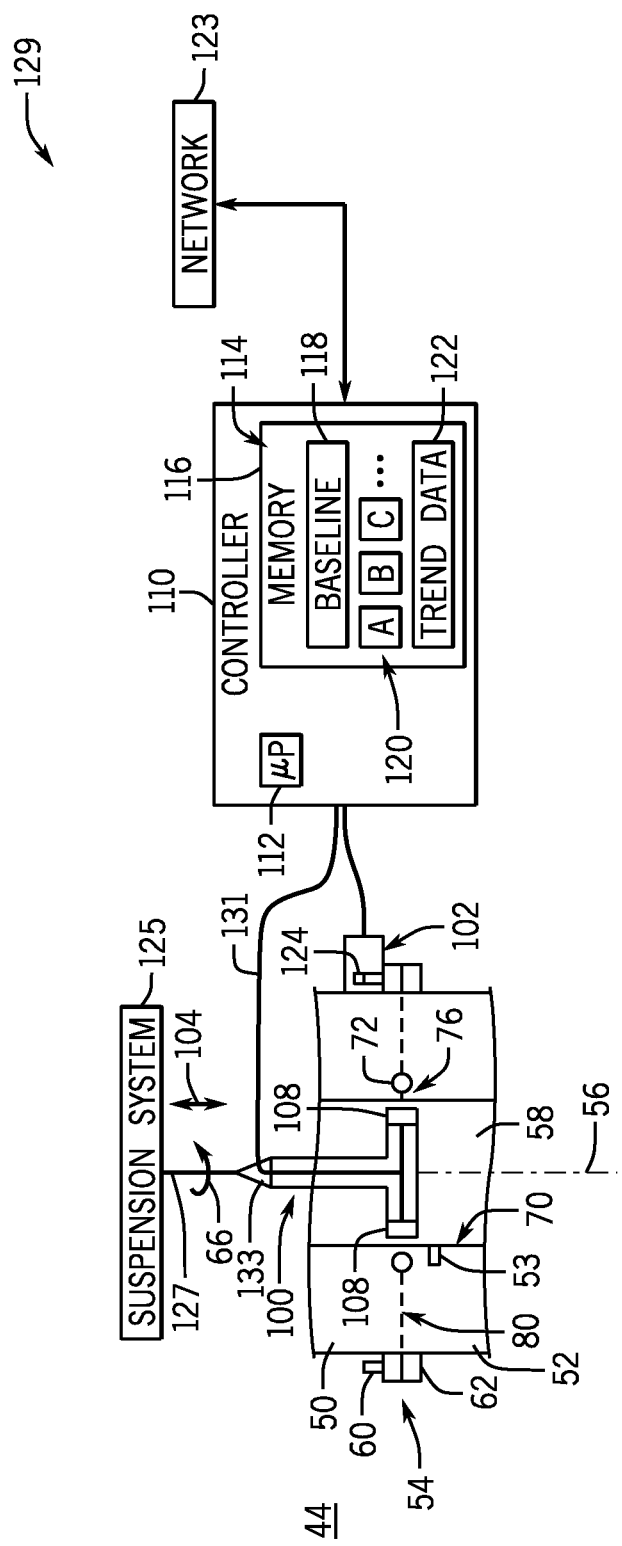
FIG. 4 is a block diagram of embodiments of probe assemblies and a flange connection.

FIG. 4 illustrates embodiments of a first probe assembly 100 (e.g., bore probe assembly, flange probe assembly) and a second probe assembly 102 (e.g., bolt probe assembly) that are configured to inspect portions of the first and second components 50, 52. The first probe assembly 100 is disposed within the bore 58 of the first and second components 50, 52 along the axis 56. The first probe assembly 100 is moved in an axial direction 104 along the bore 58 to inspect axial portions of the first and second components 50, 52, and the first probe assembly 100 is rotated in the circumferential direction 66 to inspect circumferential portions of the first and second components 50, 52. One or more probes 108 (e.g., ultrasound probes) coupled to a controller 110 obtain inspection data regarding portions of the first and second components 50, 52 adjacent to the one or more probes 108. The one or more probes 108 may be in contact with the interior surfaces 70 of the bore 58 to obtain the inspection data. In some embodiments, the one or more probes 108 emit ultrasound signals into the first and second components 50, 52, and the one or more probes 108 receive reflected ultrasound signals. Each probe 108 may include one or more transducers. A couplant medium (e.g., water, oil, lubricant) may be disposed between the one or more probes 108 and the interior surfaces 70 of the bore 58 such that the one or more probes 108 are in contact with the interior surfaces 70 via the couplant medium. The couplant medium may be applied (e.g., injected, pumped, sprayed) to the surface of the one or more probes 108, the interior surfaces 70 of the bore 58, or any combination thereof. The couplant medium may facilitate transmission of the ultrasound signals between the one or more probes 108 and the interior surfaces 70 of the first and second components 50, 52. The one or more probes 108 emit the ultrasound signals in the radial direction 73 into the first and second components 50, 52.

A processor 112 of the controller 110 may process signals based at least in part on the received signals to generate the inspection data 114 that may be stored in a memory 116. The inspection data 114 may include, but is not limited to baseline data 118, inspection run data 120, and trend data 122. The baseline data 118 may be used for comparison with later obtained inspection run data 120 to determine any deviations from a baseline (e.g., zero reference). The baseline data 118 may be based at least in part on a model, or the baseline data 118 may be empirically determined. For example, the baseline data 118 may be empirically determined from components 50, 52 of an assembled flange connection 54 after manufacture or refurbishment. The inspection run data 120 is based at least in part on signals processed by the processor 112 for a particular inspection run, such as a re-inspection prior to installation of the first and second components 50, 52 in a second hydrocarbon extraction system. The inspection run data 120 may be compared with the baseline data 118 to identify and evaluate any flaws (e.g., porosity, cracks, wear) of the components 50, 52. The processor 112 may generate the trend data 122 upon comparison of one or more sets of the inspection run data 120 with previously obtained sets of the inspection run data 120. In some embodiments, trend data 122 may be based at least in part on comparison of inspection run data 120 from different components, different hydrocarbon extraction systems, or any combination thereof. Accordingly, the trend data 122 may facilitate the identification of trends or patterns in cracks or wear of components of the hydrocarbon extraction system.

In some embodiments, the inspection data 114 may include identifying information regarding the inspected component (e.g., part number, flange connection identifier, RFID, installation history) and the inspection process (e.g., inspection operator, date, time). Furthermore, some of the inspection data 114 may be stored on and/or accessed from a network 123 remote from the controller 110. As may be appreciated, the network 123 may facilitate the communication of inspection data 114 between controllers 110 at different locations.

In some embodiments, a suspension system 125 coupled to the first probe assembly 100 moves the first probe assembly 100 in the axial direction 104 within the bore 58. The first probe assembly 100 may be suspended by one or more cables 127 coupled to the suspension system 125. In some embodiments, the suspension system 125 includes one or more winches or pulleys coupled to the one or more cables 127 to facilitate movement in the axial direction 104. The suspension system 125 may couple to the stack equipment 18 such that the one or more cables 127 are suspended proximate to the axis 56 of the bore 58. One or more umbilical lines 131 couple the first probe assembly 100 to the controller 110. Each umbilical line of the one or more umbilical lines 131 may convey electrical signals, electrical power, or fluids between the controller 110 and the first probe assembly 100. A connection receiver 133 of the first probe assembly 100 may be configured to couple the one or more umbilical lines 131 with corresponding conduits of the first probe assembly 100 via one or more quick connections. While the suspension system 125 and the controller 110 are illustrated in FIG. 4 as separate components of an inspection system 129, it may be appreciated that some embodiments of the suspension system 125 may be integrated with the controller 110, such as being disposed within a common enclosure.

The second probe assembly 102 utilizes one or more fastener probes 124 to generate inspection data regarding the plurality of fasteners 60 of the flange connection 54. The one or more fastener probes 124 emit ultrasound signals into the fasteners 60 in the axial direction 104, and the one or more fastener probes 124 receive reflected ultrasound signals. In some embodiments, the one or more fastener probes 124 emit ultrasound signals in a direction substantially parallel (e.g., less than 30° offset) to the axial direction 104. As may be appreciated, the one or more fastener probes 124 may be in contact with a fastener 60 (e.g., bolt, stud) when emitting and receiving the ultrasound signals. In a similar manner as discussed above with the one or more probes 108, the controller 110 may process signals based at least in part on the received signals to generate the inspection data 114 that may be stored in the memory 116. The inspection data 114 may be associated with each respective fastener 60 of the plurality of fasteners. In some embodiments, each fastener probe 124 may rotate about a fastener axis to obtain the inspection data for each fastener 60. Accordingly, the inspection data 114 for each fastener of the flange connection 54 may be obtained in series via the second probe assembly 102. Multiple second probe assemblies 102 may facilitate obtaining inspection data for multiple respective fasteners 60 in parallel with one another.

Figure 5:
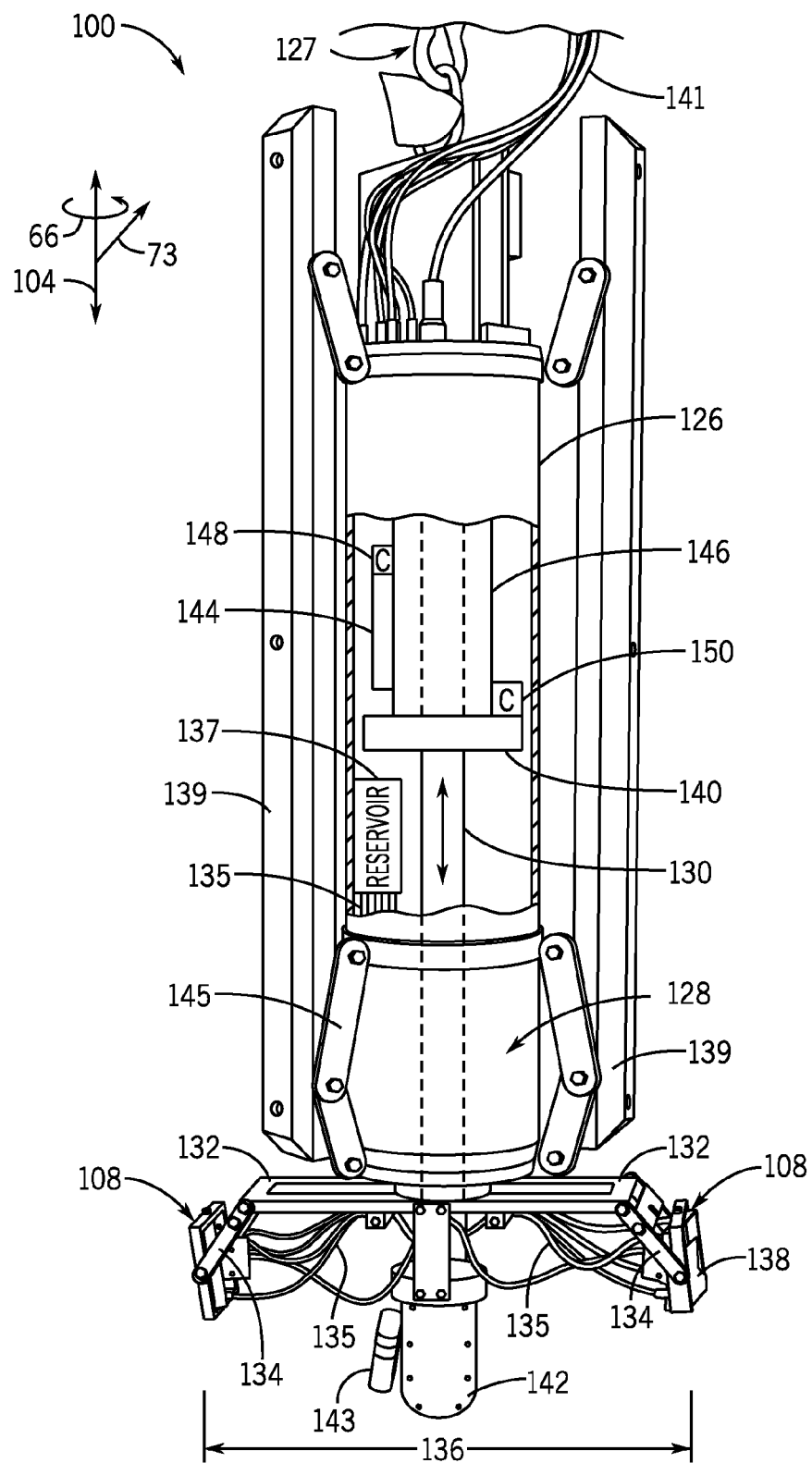
FIG. 5 is a side view of an embodiment of a probe assembly.

FIG. 5 is a side view of an embodiment of the first probe assembly 100 configured to inspect the components of an assembled flange connection 54 from the bore 68. The first probe assembly 100 may include a shell 126 that at least partially encloses components of the first probe assembly 100. In some embodiments, the shell 126 is a tubular member with an anodized exterior surface 127 that may increase the corrosion resistance of the shell 126. One or more probes 108 (e.g., ultrasound transducers) are radially disposed about a shaft 130 that may be inserted into the bore 58 of an assembled flange connection 54. The shaft 130 of the first probe assembly 100 may be substantially aligned with the axis 56 of the flange connection 54 so that the probes 108 are concentrically arranged about the axis 56. In some embodiments, portions of the shaft 130 are threaded to facilitate controlled circumferential and axial movement of the shaft. The one or more probes 108 may include, but are not limited, to a phased array of ultrasound transducers. Embodiments of the first probe assembly 100 may have 1, 2, 3, 4, 5, 6, 7, 8, 9, 10, or more probes 108. The probes 108 may be uniformly spaced apart from each other in the circumferential direction 66 about the shaft 130. Each probe 108 is coupled to an arm 132 extending in a radial direction 73 from the shaft 130. In some embodiments, a movable segment 134 of one or more arms 132 may be moved (e.g., extended, folded, retracted) to adjust a diameter 136 of the first probe assembly 100, such as to facilitate insertion into the bore 58. In some embodiments, the movable segment 134 for each probe 108 may be separately controlled (e.g., extended, retracted).

During an inspection, the one or more probes 108 may be urged into contact with the interior surface 70 of the bore 58. For example, the movable segments 134 may be moved such that a transducer surface 138 of each probe 108 interfaces with the interior surface 70. As discussed above, the transducer surface 138 of each probe 108 may interface with the interior surface 70 via a couplant medium. In some embodiments, centering fixtures 139 interface with the interior surface 70 of the bore 58 to center the shaft 130 along the axis 56 of the flange connection 54. Linkages 145 coupled between the centering fixtures 139 and the shell 126 may be controlled to extend or retract radially to adjust the lateral position of the first probe assembly 100 within the bore 58. Accordingly, the linkages 145 and the centering fixtures 139 may be controlled to align the shaft 130 with the axis 56 through the bore 58. As may be appreciated, the ultrasound signals emitted and received by the one or more probes 108 may enable the identification and measurement of flaws (e.g., porosity, cracks, wear) at the surface (e.g., interior surface 70) adjacent the one or more probes. Additionally, or in the alternative, the ultrasound signals emitted and received by the one or more probes 108 may enable the identification and measurement of flaws beneath the surface 70 of the bore 58, such as in the lip portion 76, the seal passage 72, the seal 74, or the body of the components radially outward from the seal passage 72, or any combination thereof.

One or more fluid conduits 135 may supply respective fluids (e.g., couplant medium, air) to the arms 132, to the one or more probes 108, to the interior surface 70 of the bore 58, or any combination thereof. In some embodiments, one or more reservoirs 137 of the first probe assembly 100 supply respective fluids to the fluid conduits 135. The one or more reservoirs 137 may be internal to the shell 126 of the first probe assembly 100. Additionally, or in the alternative, supply conduits 141 supply fluids to the first probe assembly 100 and the fluid conduits 135 from an upstream source that may be outside the bore 58. In some embodiments, the supply conduits 141 supply fluids to actuate pneumatic or hydraulic components of the first probe assembly 100, such as the movable segments 134, centering fixtures 139 (e.g., skids), or controls for axial and circumferential movement of the one or more probes 108 within the bore 58, or any combination thereof. In some embodiments, one or more supply conduits 141 supplies electrical power to components of the first probe assembly 100. Some fluid conduits 135 supply the couplant medium to the one or more probes 108 and/or to the interior surface 70 to facilitate the transmission of ultrasound signals between the one or more probes 108 and the interior surface 70. The couplant medium may include, but is not limited to, water, oil, lubricant, or any combination thereof. In some embodiments, air may be supplied to the arms 132, the one or more probes 108, or the interior surface 70 to remove debris or other materials from the interior surface 70.

Rotating the shaft 130 in the circumferential direction 66 moves the one or more probes 108 across the interior surface 70 of the bore 58 in a generally circumferential path. In this manner, the first probe assembly 100 may obtain inspection data for portions of the first component 50 and the second component 52 along the circumferential path. A rotary encoder 140 coupled to the shaft 130 enables the controller 110 to determine the circumferential position of each probe 108 during an inspection. Accordingly, the controller 110 may associate the inspection data along the circumferential path with the circumferential position of each probe 108 to identify the circumferential position of identified features in the inspection data. In some embodiments, the inspection data along the circumferential path may be based at least in part on an identified circumferential reference point (e.g., zero point) of the bore 58. The circumferential reference point may be utilized to calibrate the inspection data among different inspection runs to facilitate comparison of the inspection data. The circumferential reference point may include, but is not limited to a feature on the interior surface 70, a feature embedded in the flange connection 54, an RFID tag (e.g., first identifier 51, second identifier 53), or any combination thereof. In some embodiments, a camera 143 may be mounted to the shaft via a camera connection 142 to visually identify the circumferential reference point on the interior surface 70. Additionally, or in the alternative, another sensor (e.g., RFID reader) may be coupled to the camera connection 142 to identify the circumferential reference point within the bore 58 to calibrate the inspection data. That is, the first identifier 51 or the second identifier 53 may correspond to the circumferential reference point. Moreover, in some embodiments, the first probe assembly 100 may be inserted into the bore 58 with a known reference orientation.

Moving the shaft 130 in the axial direction 104 moves the one or more probes 108 across the interior surface 70 of the bore 58 in a generally axial path. In this manner, the first probe assembly 100 may obtain inspection data for portions of the first component 50 and the second component 52 at various axial positions along the axial path. A vertical encoder 144 coupled to the shaft 130 of the first probe assembly 100 enables the controller 110 to determine the axial position of each probe 108 during an inspection. Accordingly, the controller 110 may associate the inspection data along the axial path with the axial position of each probe 108 to identify the axial position of identified features in the inspection data. The inspection data along the axial path may be based at least in part on the identified circumferential reference point at a known axial position, or a separate axial reference point.

The inspection data from the one or more probes 108 along multiple circumferential and axial paths may be utilized to form a model (e.g., 3D model) of the components 50, 52 of the flange connection 54. Various combinations of axial and circumferential paths of the one or more probes 108 through the bore 58 may be utilized to form the model. For example, upon identification of a first axial location (e.g., seal interface between the components 50, 52) via the camera 143, the one or more probes 108 may be moved along a first circumferential path that spans an axial length of the first axial location, moved along a second circumferential path adjacently upstream of the first circumferential path, and moved along a third circumferential path adjacently downstream of the first circumferential path. That is, the one or more probes 108 may be moved along three adjacent circumferential paths of the bore 58 bracketing the identified first axial location (e.g., the seal interface). Accordingly, the one or more probes 108 may transmit and receive ultrasound signals with the seal 74 between the components 50, 52.

In some embodiments, the shaft 130 is coupled to a mounting shaft 146 via a threaded connection. That is, the shaft 130 may be threaded on an upstream end of the shaft 130, and rotating the shaft 130 in the circumferential direction 66 also moves the one or more probes 108 in the axial direction 104 as the shaft 130 progresses or regresses via threads relative to the downstream end of the mounting shaft 146. Accordingly, the one or more probes 108 may move in the circumferential direction 66 and the axial direction 104 substantially simultaneously. The number of rotations of the first probe assembly 100 utilized to inspect a section of the bore 58 proximate to a flange connection 54 may be based at least in part on the quantity of probes 108, the sensing area of the probes 108, and an axial length of the section of the bore 58 to be inspected, or any combination thereof.

A first control 148 coupled to the shaft 130 may control the movement of the one or more probes 108 in the axial direction 104, and a second control 150 coupled to the shaft 130 may control the movement of the one or more probes 108 in the circumferential direction 66. The controller 110 may control the axial and circumferential movement of the one or more probes 108 via the first and second controls 148, 150. In some embodiments, the movement of the one or more probes 108 in the axial and circumferential directions is controlled via the first control 148. Each of the first and second controls 148, 150 may include, but is not limited to, an electric motor, a hydraulic motor, or a pneumatic motor. Arrangements of the first and second controls 148, 150 within the shell 126 may protect the first and second controls 148, 150 and the supply conduits 135 from the external environment, thereby reducing wear on such components when the first probe assembly 100 is inserted and removed from the bore 58. In some embodiments, the first and second controls 148, 150 may be controlled to execute routines to inspect one or more predetermined circumferential paths along the interior surface 70 of the bore 58. Additionally, or in the alternative, the circumferential and axial movement of the one or more probes 108 within the bore 58 may be manually controlled.

Figure 6:
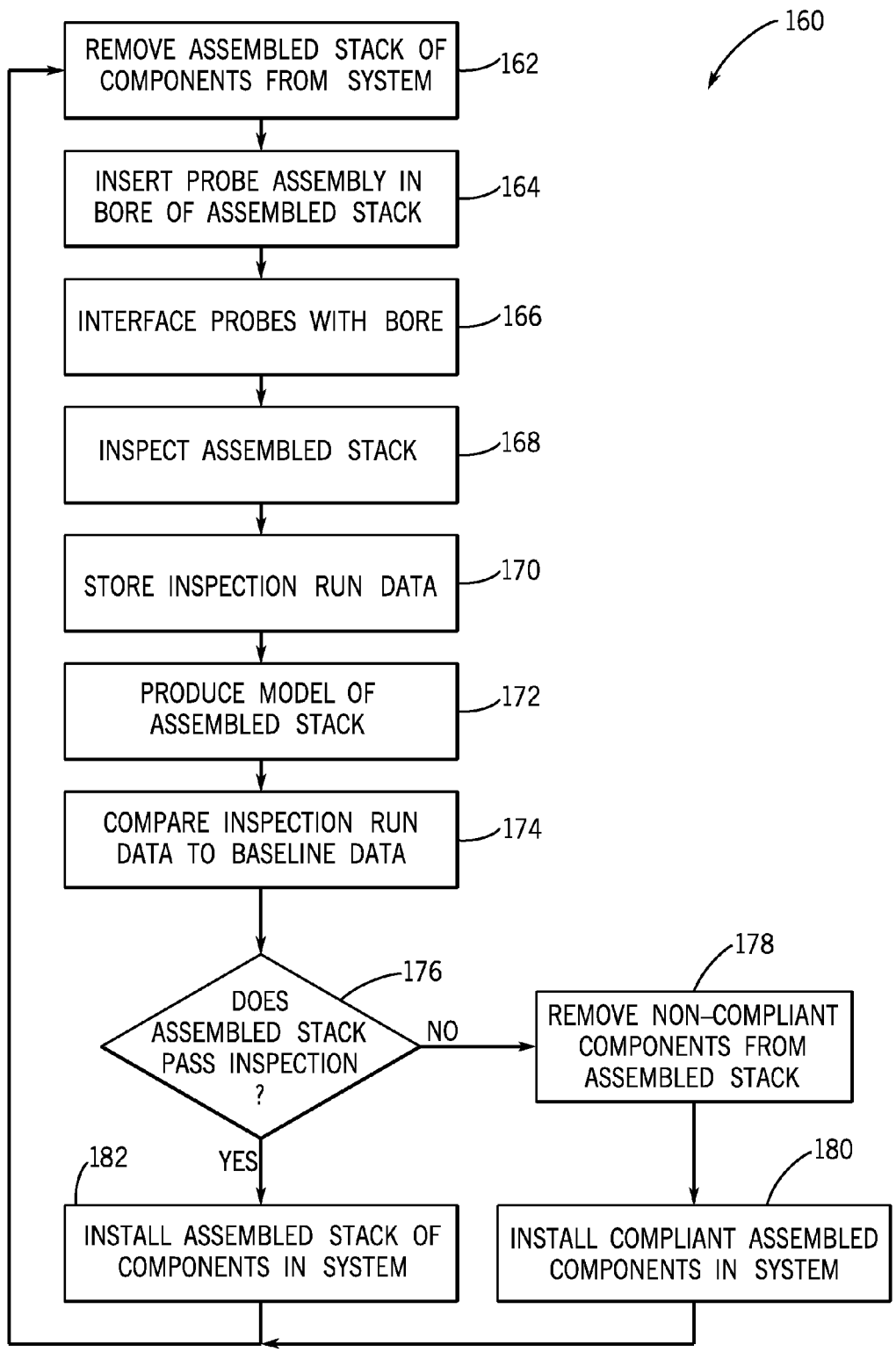
FIG. 6 is an embodiment of a method for inspecting a flange connection of an assembled stack of components.

FIG. 6 is an embodiment of a method 160 for inspecting a flange connection of an assembled stack of components. The assembled stack of components is removed (block 162) from a system (e.g., hydrocarbon extraction system). The assembled stack may include two or more components coupled to one another via a flange connection as discussed above. For example, components of the assembled stack may include, but are not limited to, a lower marine riser package, one or more blowout preventers (BOPs), a subsea manifold, production trees, an H-4® subsea connector, or any combination thereof. In some embodiments, the assembled stack is removed from a subsea environment to the surface of a drilling rig or a ship. Once removed from the system, the first probe assembly is inserted (block 164) into a bore of the assembled stack, and one or more probes of the first probe assembly are interfaced (block 166) with the bore for inspection. As discussed above, the one or more probes may include, but are not limited to ultrasound probes that are configured to emit and receive ultrasound signals. Moreover, each of the one or more ultrasound probes may be a phased array of ultrasound transducers. Additionally, the couplant medium (e.g., water, oil, lubricant) may be disposed between the one or more probes and the interior surfaces of the bore such that the one or more probes are in contact with the interior surfaces via the couplant medium.

The first probe assembly is moved axially and circumferentially through the bore to inspect (block 168) the assembled stack of components and the one or more flange connections between the assembled components. The first probe assembly is configured to inspect the assembled stack without disassembling components from the stack. That is, one or more flange connections between components are inspected while the respective components are secured together via the flange connections. The controller coupled to the first probe assembly stores (block 170) inspection run data generated during the inspection (block 168). The stored inspection run data may identify features of portions (e.g., interior surface, lip portion, seal passage, seal) of the components of the inspected flange connection. In some embodiments, the inspection run data may identify the axial and/or circumferential location of identified features of the components relative to a reference point. In some embodiments, the controller produces (block 172) a model of the assembled stack based at least in part on the inspection run data. The model may enable the inspection run data to be readily understood and conveyed by inspection technicians, thereby facilitating the identification of flaws, such as porosity, cracks, wear, or any combination thereof.

The controller may also compare (block 174) the inspection run data to baseline data. The comparison may enable the controller or an operator to determine (node 176) whether the assembled stack passes inspection. If any of the components of the assembled stack do not pass inspection, non-compliant components may be removed (block 178) from the assembled stack so that the assembled components that pass the inspection may be installed (block 180) into another system. If the assembled stack passes inspection, then the entire assembled stack may be installed (block 182) into another system. Accordingly, the method 160 enables the inspection of an assembled stack of components and the corresponding flange connections without unnecessarily disassembling the components, thereby reducing the inspection time and inspection costs.

This written description uses examples to disclose the embodiments, including the best mode, and also to enable any person skilled in the art to practice the present disclosure, including making and using any devices or systems and performing any incorporated methods. The patentable scope of the present disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A system comprising:
a probe assembly configured to inspect components of an assembled flange connection when the probe assembly is disposed within a bore of the components, wherein the probe assembly comprises:
a shaft configured to be aligned with an axis of the assembled flange connection;
one or more ultrasound probes coupled to the shaft, wherein the one or more ultrasound probes are configured to interface with an interior surface of the bore of the components, to emit ultrasound signals into the components, and to receive ultrasound signals from the components;
one or more encoders coupled to the shaft and configured to determine a position of the one or more ultrasound probes relative to a reference point of the assembled flange connection during an inspection of the components of the assembled flange connection; and
a first control coupled to the shaft, wherein the first control is configured to control movement of the one or more ultrasound probes in an axial direction along the axis of the assembled flange connection.

2. The system of claim 1, wherein the probe assembly comprises an arm disposed between the shaft and a first ultrasound probe of the one or more ultrasound probes, wherein the arm comprises a movable segment configured to adjust radially relative to the axis to interface the first ultrasound probe with the interior surface of the bore.

3. The system of claim 2, wherein the probe assembly comprises centering fixtures configured to adjust radially to align the shaft with the axis.

4. The system of claim 1, wherein the probe assembly comprises a second control coupled to the shaft, wherein the second control is configured to move the one or more ultrasound probes in a circumferential direction along a desired path of the interior surface of the bore of the components.

5. The system of claim 4, wherein the desired path comprises movement in the circumferential direction at an axial position of the bore that corresponds to a seal interface between the components of the assembled flange connection.

6. The system of claim 4, wherein the desired path comprises substantially simultaneous movement in the axial direction and movement in the circumferential direction.

7. The system of claim 1, comprising a controller configured to generate a model of the assembled flange based at least in part on the ultrasound signals received by the one or more ultrasound probes and the corresponding position of the one or more ultrasound probes when the ultrasound signals are received.

8. The system of claim 1, wherein the probe assembly comprises a camera coupled to the shaft, wherein the camera is configured to identify the reference point of the assembled flange connection.

9. The system of claim 1, wherein the probe assembly comprises a sensor configured to detect a radio frequency identification tag corresponding to the reference point of the assembled flange connection.

10. The system of claim 1, wherein the probe assembly comprises a shell, the shaft is disposed at least partially within the shell, the one or more probes are disposed outside the shell, and the one or more encoders are disposed within the shell.

11. A controller coupled to a probe assembly configured to be disposed within a bore of an assembled flange connection, wherein the controller is configured to control axial movement of the probe assembly within the bore of the assembled flange connection, to control circumferential movement of the probe assembly within the bore of the assembled flange connection, and to control an ultrasound inspection of an interior surface of the bore, wherein the ultrasound inspection comprises emitting ultrasound signals from one or more probes of the probe assembly into the components, receiving ultrasound signals with the one or more probes of the probe assembly, and comparing the received ultrasound signals to baseline data for the assembled flange connection.

12. The controller of claim 11, wherein the controller is configured to control an alignment of the probe assembly within the bore via control of centering fixtures configured to interface with the interior surface of the bore.

13. The controller of claim 11, wherein the controller is configured to generate a model of the assembled flange based at least in part on the ultrasound signals received by the one or more ultrasound probes and the corresponding position of the one or more ultrasound probes when the ultrasound signals are received.

14. The controller of claim 11, wherein the controller is configured to identify a reference point at an axial position of the bore, and to control the one or more probes to move in a circumferential direction along the interior surface at the axial position.

15. An inspection method comprising:
inserting a probe assembly into a bore of an assembled stack of components from a hydrocarbon extraction system, wherein the assembled stack of components comprises an assembled flange connection between the components;
emitting ultrasound signals from the probe assembly into the components of the assembled stack;
receiving ultrasound signals at the probe assembly, wherein the received ultrasound signals are reflected from the components of the assembled stack; and
generating a model of the assembled flange connection of the assembled stack based at least in part on the received ultrasound signals.

16. The inspection method of claim 15, comprising locating a reference point of the assembled flange connection at an axial location along the bore, wherein the probe assembly is axially positioned within the bore such that the emitted ultrasound signals are emitted at the axial location and the received ultrasound signals are received at the axial location.

17. The inspection method of claim 15, comprising rotating one or more ultrasound probes of the probe assembly within the bore while emitting and receiving ultrasound signals.

18. The inspection method of claim 17, comprising radially extending the one or more ultrasound probes of the probe assembly to interface with an interior surface of the bore prior to rotating the one or more ultrasound probes.

19. The inspection method of claim 15, comprising identifying flaws in components of the assembled stack based at least in part on the received ultrasound signals without disassembling the assembled flange connection.

20. The inspection method of claim 15, comprising certifying the assembled stack of components for installation in another hydrocarbon extraction system without disassembling the assembled flange connection.

* * * * *